US011096913B2

(12) United States Patent
Fossati et al.

(10) Patent No.: US 11,096,913 B2
(45) Date of Patent: *Aug. 24, 2021

(54) HIGH-STABILITY PACKAGED SOLUTIONS OF T4 THYROID HORMONE

(71) Applicant: ALTERGON SA, Lugano (CH)

(72) Inventors: Tiziano Fossati, Moltrasio (IT); Lorenzo Bellorini, Comerio (IT); Marco Pizzutti, Sorengo (CH)

(73) Assignee: ALTERGON SA, Lugano (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/697,924

(22) Filed: Nov. 27, 2019

(65) Prior Publication Data
US 2020/0101033 A1 Apr. 2, 2020

Related U.S. Application Data

(63) Continuation of application No. 15/445,900, filed on Feb. 28, 2017, now Pat. No. 10,537,538.

(60) Provisional application No. 62/437,624, filed on Dec. 21, 2016.

(30) Foreign Application Priority Data

Oct. 18, 2016 (EP) .................................... 16194294

(51) Int. Cl.
A61K 31/195 (2006.01)
A61K 9/00 (2006.01)
A61K 31/197 (2006.01)
A61K 31/00 (2006.01)
A61K 9/06 (2006.01)
A61J 1/00 (2006.01)
A61K 47/10 (2017.01)
B65D 65/40 (2006.01)
B65D 75/30 (2006.01)
B65D 77/02 (2006.01)
A61K 31/198 (2006.01)
A61K 9/08 (2006.01)

(52) U.S. Cl.
CPC .............. A61K 31/197 (2013.01); A61J 1/00 (2013.01); A61K 9/0095 (2013.01); A61K 9/06 (2013.01); A61K 31/00 (2013.01); A61K 47/10 (2013.01); B65D 65/40 (2013.01); B65D 75/30 (2013.01); B65D 77/02 (2013.01); A61K 9/08 (2013.01); A61K 31/198 (2013.01)

(58) Field of Classification Search
CPC ................. A61K 31/198; A61K 9/08
USPC .......................... 514/567; 424/400
See application file for complete search history.

(56) References Cited

U.S. PATENT DOCUMENTS

| 3,035,974 | A | 5/1962 | Murray |
| 3,128,920 | A | 4/1964 | Volckening et al. |
| 5,951,989 | A | 9/1999 | Heymann |
| 6,458,842 | B1 | 10/2002 | Dickinson et al. |
| 7,723,390 | B2 | 5/2010 | Garavani et al. |
| 9,345,772 | B1 | 5/2016 | Parikh et al. |
| 10,537,538 | B2 * | 1/2020 | Fossati .............. B65D 77/02 |
| 2003/0050344 | A1 | 3/2003 | Garavani et al. |
| 2004/0266877 | A1 | 12/2004 | Dickinson et al. |
| 2005/0059574 | A1 | 3/2005 | Klein et al. |
| 2010/0197790 | A1 | 8/2010 | Zoppetti et al. |
| 2014/0073695 | A1 | 3/2014 | Psarrakis et al. |
| 2014/0179785 | A1 | 6/2014 | Bellorini et al. |
| 2018/0104204 | A1 | 4/2018 | Fossati et al. |
| 2018/0353432 | A1 | 12/2018 | Carucci et al. |

FOREIGN PATENT DOCUMENTS

| EP | 1291021 A2 | 3/2003 |
| GB | 2191695 A | 12/1987 |
| WO | WO 2007/077252 A1 | 7/2007 |
| WO | WO 2010/086030 A1 | 8/2010 |
| WO | WO 2012/120338 A1 | 9/2012 |
| WO | WO 2013/072304 A1 | 5/2013 |
| WO | WO 2016/137969 A2 | 9/2016 |
| WO | WO 2018/073209 A1 | 4/2018 |

OTHER PUBLICATIONS

Boulton, D. et al., Stability of an Extemporaneously Compounded Levothyroxine Sodium Oral Liquid, American journal of Health-System Pharmacy, May 15, 1996, 53(10), pp. 1157-1161.
European Patent Office, Extended European Search Report, EP Patent Application No. 16194294.1, dated Mar. 29, 2017, seven pages.
Jonklaas, J. et al., "Guidelines for the Treatment of Hypothyroidism: Prepared by the American Thyroid Association Task Force on Thyroid Hormone Replacement," Thyroid, 24(12), Dec. 12, 2014, pp. 1670-1751.
Linnoila, M. et al., "Drug interactions with alcohol," Drugs, vol. 18, 1979, p. 299-311.
PCT International Search Report and Written Opinion, PCT Application No. PCT/EP2017/076412, dated Feb. 21, 2018, ten pages.
Won, C., "Kinetics of Degradation of Levothyroxine in Aqueous Solution and in Solid State," Pharmaceutical Research 9(1), Jan. 1992, pp. 131-137.
Scavone, C. et al., "Medication adherence and the use of new pharmaceutical formulations: the case of levothyroxine," Minerva Endocrinologica, 41(2), Jun. 2016, pp. 279-289.
Anonymous, "Highlights of Prescribing Information," Dec. 2017, pp. 1-15 [Online] [Retrieved from the Internet] <URL: https://www.accessdata.fda.gov/drugsatfda Docs/label/2017/021924s013161.pdf>.

(Continued)

Primary Examiner — Shengjun Wang
(74) Attorney, Agent, or Firm — Fenwick & West LLP

(57) ABSTRACT

The invention relates to highly stable alcohol-free, water-glycerol solutions of T4 thyroid hormone, with a reduced amount of T3 impurity, packaged via specific container arrangements. The containers are multi-barrier ones, in which a number of layers of specific materials separate the solution from contact with the external environment.

9 Claims, No Drawings

(56) References Cited

OTHER PUBLICATIONS

Anonymous, "Highlights of Prescribing Information: These highlights do not include all the information needed to use TIROSINT-SOL safely and effectively. See full prescribing information for TIROSINT-SOL," Dec. 2016, pp. 1-19, [Online] [Retrieved from the Internet] <URL: https://www.accessdata.fda.gov/drugsatfdadocs/label/2016/206977s0001b1.pdf>.

Bhatnagar, S., "Calories in Black Coffee: How it Helps to Shed Extra Kilos," Jun. 12, 2018, 16 pages, [Online] [Retrieved on Oct. 13, 2020] Retrieved from the Internet <URL: https://food.ndtv.com/food-drinks/calories-in-black-coffee-how-it-helps-to-shed-extra-kilos-1866361>.

Cappelli, C. et al., "Thyroid Hormone Profile in Patients Ingesting Soft Gel Capsule or Liquid Levothyroxine Formulations with Breakfast," International Journal of Endocrinology, vol. 2016, Article ID 9043450, May 30, 2016, pp. 1-5.

Italian Patent and Trademark Office, Search Report and Opinion, IT Patent Application No. 102019000003013, Nov. 6, 2019, nine pages.

Morelli, S. et al., "Timing of breakfast does not influence therapeutic efficacy of liquid levothyroxine formulation," Endocrine, vol. 52, Nov. 4, 2015, pp. 571-578.

PCT International Search Report and Written Opinion, PCT Application No. PCT/EP2020/054873, dated Apr. 29, 2020, 12 pages.

United States Office Action, U.S. Appl. No. 16/421,373, dated Oct. 29, 2020, ten pages.

Vita, R., et al. A novel formulation of L-thyroxine (L-T4) reduces the problem of L-T4 malabsorption by coffee observed with traditional tablet formulations, Endocrine, vol. 43, Aug. 30, 2012, pp. 154-160.

Vita, R., et al. The administration of l-thyroxine as soft gel capsule or liquid solution, Expert Opinion on Drug Delivery 11:7, Jun. 4, 2014, pp. 1103-1111.

* cited by examiner

HIGH-STABILITY PACKAGED SOLUTIONS OF T4 THYROID HORMONE

This application is a continuation of co-pending U.S. application Ser. No. 15/445,900, filed Feb. 28, 2017, which claims the priority benefit of U.S. patent application Ser. No. 62/437,624, filed on Dec. 21, 2016; and European patent application no. EP 16194294, filed on Oct. 18, 2016. The contents of these applications are incorporated by reference herein in their entirety.

FIELD OF THE INVENTION

The present invention relates to the field of pharmaceutical preparations of thyroid hormones. Specifically, the invention relates to a pharmaceutical preparation of thyroid hormone T4 in an alcohol-free water-glycerol solution, suitable for oral administration and characterized by high physical, chemical and microbiological stability. The invention also relates to the use of said pharmaceutical preparation in the treatment of disorders caused by thyroid hormones deficiency.

BACKGROUND

The thyroid hormone tetraiodothyronine or thyroxine (T4) is secreted by the follicular cells of the thyroid gland in response to the pituitary-gland hormone TSH, the production of which is regulated in turn by the hypothalamic hormone TRH. The pituitary gland also secretes the T3 hormone (triiodothyronine or liothyronine). In fact, most of the T3 in the body results from conversion of T4 to T3 outside the thyroid gland. T3 is 4-5 times more potent that T4, which means that one mg of T3 has a much greater effect on the body than one mg of T4.

The secretion of thyroid hormones follows a circadian rhythm. The highest levels of T3 and T4 are reached during the night and the early hours of the morning.

T3 and T4 are essential for the normal body growth of children and for the maturation of the various body systems, especially the skeleton, and regulate metabolic activity in adults, influencing the function of every organ and tissue. In particular, T3 and T4 increase oxygen consumption at rest, raising the basal metabolism, the body temperature and the daily calories requirement. They regulate carbohydrate metabolism, promoting glycogenolysis and gluconeogenesis, and increase the activity of the enzymes involved in glucose oxidation. Thyroid hormones are involved in lipolysis and lipogenesis, regulate protein synthesis, exercising a trophic effect on the muscle, and affect the cardiovascular system.

Thyroid hormones are essential to the cardiac function: they increase myocardial contractility (positive inotropic effect), increase the heart rate (positive chronotropic effect) and increase venous return to the heart.

In general, the effect of thyroid hormones is mainly anabolic at low doses, whereas they have a catabolic action at high doses. In situations of physiological deficiency of thyroid hormones, as in the case of primary and secondary hypothyroidism, a treatment based on thyroid hormones is required, administered as such or in the form of sodium salts or hydrates. The treatment continues throughout the patient's life, and the posology (dose and frequency of administration) is customized according to the patient's response.

Selecting the dose is a critical aspect of thyroid hormone treatments: an under-dose leads to a poor response, while an excessive dose can produce toxic symptoms of hyperthyroidism such as tachycardia, sweating, weight loss, nervousness, diarrhea, bone resorption due to activation of the osteoclasts, and heart problems. It is therefore important for patients to be able to count on reliable formulations in terms of dose accuracy.

T4 and T3 hormones are conveniently administered via the oral route. Although T4 and T3 hormones are both therapeutically effective, the administration of T4 is generally preferred since T3 is too rapidly absorbed from the intestine and this rapid absorption may cause thyroid hormone toxicity (hyperthyroidism). Mixtures of T3 and T4 are also not preferred because the two hormones have different pharmacokinetic and potency, which complicates the establishment of a suitable dosage regime for the patient.

T4 hormone is conveniently administered in the form of a solution, which allows a more precise dosing as compared to solid forms. The administration of T4 solutions presents nevertheless some challenges: in fact. T4 solutions are reported to prematurely convert in part to T3 during storage. The extent of conversion is difficult to predict, since the conversion rate may be affected by a variety of environmental conditions. As a consequence, at the time of administration. T4 solutions may be contaminated with non-predictable, sometimes significant levels of T3. This causes inaccuracy of the hormone dose actually administered, with risk of overdosage due to the higher potency of T3. Due to the quite higher potency of T3 vs. T4, even a small amount of formed T3 may significantly increase the overall dosage of administered hormone, with potential consequences for the patient caused by over-dosing.

A further difficulty derives from the low water solubility of thyroid hormones, causing them to partly precipitate from solutions during storage and/or in consequence of temperature changes. A partial improvement in this area is reported in WO2010/086030, where the thyroid hormones are formulated in water-alcohol-glycerol solutions showing a good stability. The stability was further enhanced by packaging the solution within containers made of specific polymers. In an attempt to further increase stability, other packaging solutions are described in WO2013072304, wherein the water-alcohol-glycerol solution was double-packaged (i.e. contained in a plastic container which is contained in a sachet), or single-packaged in an improved multilayered plastic container. Nevertheless, under these conditions, a significant degree of instability was observed as regards to conversion of T4 into T3.

BRIEF SUMMARY OF THE INVENTION

It was now unexpectedly found that the unwanted premature conversion of T4 to T3 in packaged solution can be significantly reduced if T4 is formulated in water-glycerol, alcohol-free solutions. The invention thus relates to highly stable alcohol-free water-glycerol solutions of T4 thyroid hormone, with a reduced amount of T3 impurity, which are packaged in ready-to-use container arrangements suitable to maintain a general stability of the solution. The containers have multi-barriers, in which several layers of different materials separate the solution from contact with the external environment.

One aspect of the present invention is directed to a pharmaceutical preparation of T4 thyroid hormone, in ready-to-use packaging, consisting of a container pre-filled with an alcohol-free water-glycerol solution of hormone T4. The container is selected from:

(a) a one-component LDPE plastic container, placed in a sealed sachet consisting of laminated films made of different materials selected from the following: polyethylene, aluminium, polyethylene terephthalate, ionomer resins, paper, ethylene vinyl alcohol, copolymer resins, propylene, and fluorinated-chlorinated resins; or (b) a multi-component laminated plastic container, said container comprising multiple layers of plastic materials selected from: polyethylene, ethylene vinyl alcohol copolymer resins polyvinyl chloride, polyvinylidene chloride; polyvinyl acetate, fluorinated-chlorinated resins, ionomer resins, cyclic olefin copolymers, polyamide, polystyrene, polycarbonate, laminated metals and aluminium bonded to plastics.

In an embodiment of the invention, the T4/glycerol weight ratio in the water-glycerol solution may be in the range from about 4 to about 400 ppm.

In an embodiment of the invention, the water-glycerol solution contains less than about 2.5% of T3 impurity, or less than about 2.0% of T3 impurity, or less than about 1.8% of T3 impurity.

In an embodiment of the invention, the preparation is in a single-dose form and contains about 5 to about 350 μg T4 thyroid hormone, or about 5 to about 250 μg T4 thyroid hormone.

In an embodiment of the invention, the plastic container has a thickness of between about 150 to about 1000 μm., or between about 200 and about 800 μm.

In an embodiment of the invention, the sachet comprises laminated films selected from the group consisting of: polyethylene, aluminium and polyethylene terephthalate; polyethylene, aluminium and paper; or ionomer resins, aluminium and paper.

In an embodiment of the invention, the sachet has an overall thickness of between about 40 and about 100 μm, or between about 50 and about 90 μm.

Another aspect of the present invention is directed to a method of treating a disease associated with T3 and/or T4 hormone deficiency, the method comprising administering a pharmaceutical preparation or composition as disclosed herein to a patient in need thereof.

Another aspect of the present invention is directed to a pharmaceutical preparation comprising:
(a) a composition of an alcohol-free water/glycerol solution of T4 thyroid hormone; and
(b) a single-dose container for containing the solution;
whereby less than 2.5% of the T4 thyroid hormone in the solution converts to T3 thyroid hormone after 12 months under Long Term Storage Conditions.

In an embodiment of the pharmaceutical preparation provided herein, the conversion of T4 thyroid hormone to T3 thyroid hormone is less than for a pharmaceutical preparation in a similar single-dose container comprising a water-glycerol-alcohol solution of T4 thyroid hormone after 12 months under Long-Term Storage Conditions.

Another aspect of the present invention is directed to a pharmaceutical composition comprising an alcohol-free water/glycerol solution of T4 thyroid hormone that is capable of storage in a single-dose container, whereby the pharmaceutical composition demonstrates less than 2.5% conversion of T4 thyroid hormone to T3 thyroid hormone for 12 months under Long Term Storage Conditions.

Another aspect of the present invention is directed to a method of treating thyroid hormone deficiency comprising administering a pharmaceutical composition as provided herein to a patient in need thereof.

Another aspect of the present invention is directed to a method of treating thyroid hormone deficiency comprising administering the composition of the alcohol-free water/glycerol solution of T4 thyroid hormone provided herein to a patient in need thereof.

Another aspect of the present invention is directed to a ready-to-use pharmaceutical preparation of T4 thyroid hormone packaged in a container which is pre-filled with an alcohol-free water-glycerol solution of hormone T4, said container being selected from:
(a) a one-component LDPE plastic container, placed in a sealed sachet consisting of laminated film made of different materials selected from the following: polyethylene, aluminium, polyethylene terephthalate, ionomer resins, paper, ethylene vinyl alcohol, copolymer resins, propylene, and fluorinated-chlorinated resins; or
(b) a multi-component laminated plastic container comprising a plurality of layers of plastic materials selected from the group consisting of: polyethylene, ethylene vinyl alcohol copolymer resins, polyvinyl chloride, polyvinylidene chloride, polyvinyl acetate, fluorinated-chlorinated resins, ionomer resins, cyclic olefin copolymers, polyamide, polystyrene, polycarbonate, laminated metals, aluminium bonded to plastics, and combinations thereof.

Another aspect of the present invention is directed to a ready-to-use package of a pharmaceutical preparation of T4 thyroid hormone, the package comprising a container which is pre-filled with an alcohol-free water-glycerol solution of hormone T4, wherein the container is selected from:
(a) a one-component LDPE plastic container, placed in a sealed sachet consisting of laminated film comprising a plurality of material selected from the following: polyethylene, aluminium, polyethylene terephthalate, ionomer resins, paper, ethylene vinyl alcohol, copolymer resins, propylene, and fluorinated-chlorinated resins; or
(b) a multi-component laminated plastic container comprising a plurality of layers of plastic materials selected from the group consisting of: polyethylene, ethylene vinyl alcohol copolymer resins, polyvinyl chloride, polyvinylidene chloride, polyvinyl acetate, fluorinated-chlorinated resins, ionomer resins, cyclic olefin copolymers, polyamide, polystyrene, polycarbonate, laminated metals, aluminium bonded to plastics, and combinations thereof.

The term "about", when used in connection with any of the quantities or concentrations of a particular component in a formulation, is be understood as allowing a tolerance of ±10% of the given amount of that component, or in the tolerance of the upper and lower limits of the component.

DETAILED DESCRIPTION OF THE INVENTION

For the purpose of the present invention, the term "alcohol-free solution" means that the solution does not contain low-molecular weight alcohols. The term "low molecular weight alcohol" means an alkanol with molecular weight lower than 80 Dalton: e.g. methanol, ethanol, propane, propanediol, isopropanol, and similar alcohols; the term "alcohol-free" remains thus compatible with the presence of glycerol (which has a molecular weight of 92.1 Daltons) in the solution.

In an embodiment of the invention, the packaging used is a multi-barrier one, i.e. one in which several layers of different materials separate the solution from contact with the external environment. The layers may be part of the same container and/or may belong to different containers contained in one another, wherein the T4 solution is contained in the innermost container. In particular, the packaging can be composed according to the following options:

a. a one-component LDPE plastic container, placed in a sealed sachet consisting of laminated film made of different materials selected from the following: polyethylene, aluminium, polyethylene terephthalate, ionomer resins, paper, ethylene vinyl alcohol copolymer resins, polypropylene, and fluorinated-chlorinated resins; or b. a multi-component laminated plastic container characterized by multiple layers of plastic materials selected from polyethylene, ethylene vinyl alcohol copolymer resins, polyvinyl chloride, polyvinylidene chloride, polyvinyl acetate, fluorinated-chlorinated resins, ionomer resins, cyclic olefin copolymers, polyamide, polystyrene, polycarbonate, laminated metals, and aluminium bonded to plastics.

Preferably, the plastic container referred in (a) and/or (b) is squeezable by manual compression. Also preferably, said container referred in (a) and/or (b) has a thickness of between 150 and 1000 µm, and more preferably between 200 and 800 µm, e.g. 600 µm±15%. The above option (a) includes the variant in which more than one LDPE plastic container, each filled with the solution of T4, is contained within a single sachet containing all of them.

In one preferred embodiment of option (a), the sachet consists of laminated films made of different materials according to the following combinations: polyethylene, aluminium and polyethylene terephthalate, polyethylene, aluminium and paper, ionomer resins, aluminium and paper.

An important contribution to the stability of the T4 solution is given by the sum of thicknesses of all the films making up the sachet, i.e. the overall thickness of the sachet made of the specific laminated films mentioned above. The overall thickness should be preferably comprised within the range of 40 to 100 µm, more preferably of 50 to 90 µm. These conditions advantageously combine an effective protection from T4 degradation to T3, while avoiding using excessive packaging material. If desired, values higher than 90 µm may also be used in the present invention. Examples of the above described packaging arrangements (not in association with alcohol-free solutions of T4 hormone) are described in patent application WO2013/072304, herein incorporated by reference.

The water-glycerol solution used in the present invention can typically contain a T4:glycerol weight ratio comprised between 0.004:1000 and 0.4:1000 (i.e. 4 to 400 ppm). If the solution is formulated as a dose unit form, the suitable dose unit will typically contain from 5 to 350 µg (or preferably 5 to 250 µg) of T4 in 1 g of glycerol.

All ratios and amounts of glycerol are herein calculated based on glycerol as a pure substance. In practice however, glycerol is handled as a concentrated solution in water, typically at 85% w/w. It is thus understood that the water component of the present solutions may be derived, at least in part, from the water content of commercial glycerol. The water content of 85% glycerol is normally sufficient to obtain the solutions according to the invention. The addition of further amounts of water remains in any case possible within the scope of the invention.

The present T4 solutions contain a reduced amount of T3 impurity, where "reduced" means that T3 may be present at a maximum concentration of 2.5%, preferably 2.0%, more preferably 1.8%. Said values of T3 impurity are calculated herein as follows: (T3 µg/mL being present in the sample/T4 µg/mL being present in the sample)*100. The reduced amount of T3 impurity is a consequence of the high level of storage stability reached (in terms of limited T4 to T3 conversion), as supported in the experimental section. In particular, at the end of the stability period (25° C.±2° C./60±5% R.H.), the pharmaceutical preparation according to the invention showed a T4 content of not less than 95% of the initial concentration, and total impurities were within the standard acceptability criteria.

Moreover, the pharmaceutical preparation according to the invention has minimal or no microbiological contamination, with TAMC (total aerobic microbial count) values ≤100 CFU/g. TYMC (total yeast and mould count) values ≤10 CFU/g, and absence of *E. coli*, thus being practical to use and not susceptible to accidental contamination.

The pharmaceutical preparation according to the invention is conveniently used to treat disorders associated with thyroid hormone T3 and/or T4 deficiency. It is preferably administered orally, i.e. it is suitable for oral administration. It is noted that, although the present T4 solutions do not contain T3 (or contain it in extremely low amounts), their use extends to treat T3 deficiency since T4 is physiologically converted into T3 by the organism after administration.

A further aspect of the invention therefore relates to the use of a water-glycerol solution of thyroid hormone T4 in a packaging as described above, to prepare a medicament for the treatment of disorders associated with thyroid hormone T3 and/or T4 deficiency. The medicament is preferably suitable for oral administration.

A further aspect of the invention relates to a pharmaceutical preparation of a water-glycerol solution of thyroid hormone T4 in a packaging as described above, for use in the treatment of disorders associated with thyroid hormone T3 and/or T4 deficiency. The preparation is preferably suitable for oral administration.

A further aspect of the invention relates to a method of treating disorders associated with thyroid hormone T3 and/or T4 deficiency comprising administering a water-glycerol solution of thyroid hormone T4 packaged as described above, to a patient in need thereof. The solution is preferably suitable for oral administration.

A further aspect of the invention relates to a method of treating bariatric patients (that is, patients who undergo bariatric surgery), using the inventive package. A further aspect of the invention relates to a method of treating patients whose gastric pH is altered and thus have absorption problems or whose absorption problems may be caused by intake of food. The inventive package can be administered to such bariatric patients or such patients having altered gastric pH or altered absorption related to food intake for treatment of their respective conditions.

The present invention thus provides new packaged solutions of T4, being advantageously more stable to an unwanted premature conversion of T4 in T3 than prior solutions of T4. The increased stability ensures a more reproducible and constant amount of administered hormone, avoiding possible overdosing due to excessive administration of T3 impurities. The non-use of volatile alcohols like ethanol brings a further advantage in that the formulation does not suffer from accidental reduction of alcohol content, which reflects in an unwanted variation of hormone solubility/stability of the solution. Furthermore, the absence of such alcohols in the present water-glycerol solutions did not substantially change the overall stability of the solution in terms of T4 potency, total impurities and microbial contamination, thus resulting in a preparation meeting all the acceptability criteria for pharmaceutical use. The use of the single dose container protected by an envelope defends the product from microbiological contamination; the specific alcohol-free and preservative-free formulation is particularly indicated for chronic use.

EXPERIMENTALS

The following acronyms are herein used: polyethylene (PE), polyethylene terephthalate (PET), ethylene vinyl alcohol copolymer resins (EVOH), polyvinyl chloride (PVC), polyvinylidene chloride (PVdC), polyvinyl acetate (PVA), cyclic olefin copolymers (COC), polyamides (PA), polystyrene (PS), and polycarbonate (PC).

Example 1: Water-Ethanol-Glycerol T4 Solution (Reference)

A reference formulation was prepared in accordance with example 1 of WO2013/072304. Accordingly, one liter of a water-alcohol solution containing 100 µg/mL of T4 was prepared as follows, using the qualitative/quantitative composition listed below:

| | | | |
|---|---|---|---|
| i. | T4 | | 0.105 g |
| ii. | ethanol (96%) | | 243 g |
| iii. | glycerol (85%) | | 861 g |

The T4 was solubilized in ethanol in a suitable dissolver apparatus, under continuous stirring at ambient temperature. When a clear solution free of visible non-solubilized residues was obtained, glycerol was added, and a homogenous, clear, colourless solution was obtained under gentle stirring at ambient temperature. The solution was filtered (0.8 µm), and was then ready for packaging. The final T4 concentration in solution was 100 µg/mL. Following the same method, further solutions were prepared having the final concentrations of 25 µg/mL. 50 µg/mL. 75 µg/mL.

The packaging arrangement was made according to example 3 of WO2013/072304 as follows: a single-dose container with a nominal volume of 1.10 mL made of one-component LDPE plastic (600 µm thick) was placed in a sealed sachet (PET/Al/PE). The characteristics of the sachet were as follows:
1. Stratified film with high gas and light barrier:
2. Polyethylene terephthalate: 12 µm film thickness (value to be considered ±5-6%);
3. Al: 9 µm film thickness (value to be considered ±5-6%);
4. Polyethylene: 50 µm film thickness (value to be considered ±5-6%);
5. Overall thickness: 71 µm;
6. Oxygen permeability: 0.1-0.2 cc/m²/day; and
7. Water vapor permeability: 0.1-0.2 g/m²/day.

The oxygen permeability was measured in accordance with ASTM Standard D-3985. The water permeability was measured in accordance with ASTM Standard E-398. The prototypes were prepared on a laboratory scale, using an automatic pipette (Gilson P-1000) to fill disposable containers with 1.1 mL of the water-glycerol-ethanol solution previously described, after which the containers were sealed with a Pentaseal-lab benchtop sealing machine. They were then packaged in a hermetically sealed sachet of the type described above.

Example 2: Water-Glycerol T4 Solution

A number of solutions were prepared according to the previous reference Example 1, replacing the water-ethanol-glycerol solution described therein with the alcohol-free water-glycerol solution in accordance with the present invention. Accordingly, the following amounts of T4 hormone were dissolved in 1.222 g of glycerol 85%: 25 µg, 50 µg, 75 µg, and 100 µg, obtaining the respective final concentrations of: 25 µg/mL, 50 µg/mL, 75 µg/mL, and 100 µg/mL.

Packaging arrangement: a single-dose container with a nominal volume of 1.10 mL made of one-component LDPE plastic (600 µm thick) was placed in a sealed sachet (PET/Al/PE). Characteristics of sachet: Stratified film with high gas and light barrier: Polyethylene terephthalate: 12 µm layer thickness; Al, 12 µm layer thickness; Polyethylene 45 µm layer thickness (all values to be considered ±5-6%); Overall thickness: 69 µm.

Example 3: Storage Stability Studies

The packaged solutions obtained in the previous examples 1 and 2 were subjected to storage stability testing with the aim, in particular, to evaluate the extent of conversion of T4 in T3 during storage, under both normal or accelerated conditions. The sealed sachets were thus placed in suitable environmental test chambers, and immediately underwent a stability study under ICH conditions. The equipment used was calibrated and instantly monitored for correct operation. The following tables show the compared performances of the products obtained in Examples 1 and 2.

TABLE 1

T4 solutions 25 µg/mL - Stability Data under Long Term Conditions (25° C. ± 2° C./60% ± 5% R.H.): percent of T4→T3 conversion

| Sample | Acceptance limit (%) | 3 m (%) | 6 m (%) | 9 m (%) | 12 m(%) | 18 m(%) |
|---|---|---|---|---|---|---|
| Example 1 (reference) | ≤2.5 | 0.3 | 0.5 | 0.8 | 1.0 | 1.5 |
| Example 2 (invention) | ≤2.5% | 1.0 | 0.7 | 0.7 | 0.7 | 1.1 |

TABLE 2

T4 solutions 25 µg/mL - Stability Data under Intermediate Term Conditions (30° C. ± 2° C./65% ± 5% R.H.): percent of T4→T3 conversion

| Sample | Acceptance limit (%) | 3 m (%) | 6 m (%) | 9 m (%) | 12 m (%) |
|---|---|---|---|---|---|
| Example 1 (reference) | ≤2.5 | 0.3 | 0.5 | 0.8 | 1.0 |
| Example 2 (invention) | ≤2.5% | 0.7 | 0.9 | 1.3 | 0.8 |

TABLE 3

T4 solutions 50 µg/mL - Stability Data under Long Term Conditions (25° C. ± 2° C./60% ± 5% R.H.): percent of T4→T3 conversion

| Sample | Acceptance limit (%) | 3 m (%) | 6 m (%) | 9 m (%) | 12 m(%) | 18 m(%) |
|---|---|---|---|---|---|---|
| Example 1 (reference) | ≤2.5 | 0.5 | 1.2 | 1.3 | 1.5 | 2.1 |
| Example 2 (invention) | ≤2.5% | 0.5 | 0.7 | 0.8 | 0.9 | 1.4 |

TABLE 4

T4 solutions 50 μg/mL - Stability Data under Intermediate Term Conditions (30° C. ± 2° C./65% ± 5% R.H.): percent of T4→T3 conversion

| Sample | Acceptance limit (%) | 3 m (%) | 6 m (%) | 9 m (%) | 12 m (%) |
|---|---|---|---|---|---|
| Example 1 (reference) | ≤2.5 | 1.1 | 1.8 | 2.0 | 2.4 |
| Example 2 (invention) | ≤2.5% | 0.6 | 1.2 | 1.7 | 2.2 |

TABLE 5

T4 solutions 75 μg/mL - Stability Data under Long Term Conditions (25° C. ± 2° C./60% ± 5% R.H.): percent of T4→T3 conversion

| Sample | Acceptance limit (%) | 3 m (%) | 6 m (%) | 9 m (%) | 12 m(%) | 18 m(%) |
|---|---|---|---|---|---|---|
| Example 1 (reference) | ≤2.5 | 1.1 | 1.0 | 1.2 | 1.4 | 1.8 |
| Example 2 (invention) | ≤2.5% | 0.5 | 0.8 | 0.9 | 1.0 | 1.5 |

TABLE 6

T4 solutions 75 μg/mL - Stability Data under Intermediate Term Conditions (30° C. ± 2° C./65% ± 5% R.H.): percent of T4→T3 conversion

| Sample | Acceptance limit (%) | 3 m (%) | 6 m (%) | 9 m (%) | 12 m (%) |
|---|---|---|---|---|---|
| Example 1 (reference) | ≤2.5 | 1.3 | 2.2 | 2.4 | 2.6 |
| Example 2 (invention) | ≤2.5% | 0.7 | 1.3 | 1.8 | 2.3 |

TABLE 7

T4 solutions 100 μg/mL - Stability Data under Long Term Conditions (25° C. ± 2° C./60% ± 5% R.H.): percent of T4→T3 conversion

| Sample | Acceptance limit (%) | 3 m (%) | 6 m (%) | 9 m (%) | 12 m(%) | 18 m(%) |
|---|---|---|---|---|---|---|
| Example 1 (reference) | ≤2.5 | 0.5 | 1.0 | 1.3 | 1.5 | 2.2 |
| Example 2 (invention) | ≤2.5% | 0.5 | 0.8 | 0.8 | 1.0 | 1.4 |

TABLE 8

T4 solutions 100 μg/mL - Stability Data under Intermediate Term Conditions (30° C. ± 2° C./65% ± 5% R.H.): percent of T4→T3 conversion

| Sample | Acceptance limit (%) | 3 m (%) | 6 m (%) | 9 m (%) | 12 m (%) |
|---|---|---|---|---|---|
| Example 1 (reference) | ≤2.5 | 1.1 | 1.9 | 2.4 | 2.8 |
| Example 2 (invention) | ≤2.5% | 0.7 | 1.4 | 1.9 | 2.2 |

Example 4: Binary Experiments with Glycerol and Water

In binary experiments, T4 solutions were prepared in glycerol:water mixtures with 30:70 w/w, 50:50 w/w, 70:30 w/w and 85:15 w/w ratios. T4 was also dissolved in 100% pure glycerol. The behaviour of such T4 preparations was investigated by assessing T4 solubility, as well as chemical and microbiological stability.

The results of T4 solubility and chemical stability in accelerated conditions (40° C.±2° C./75%±5% R.H.) are reported in the tables below. T4 was added in all preparations at the highest intended concentration of 200 μg/mL. The preparations were stirred up to 40 minutes at room temperature.

TABLE 9

T4 solubility and chemical stability in accelerated conditions (40° C. ± 2° C./75% ± 5% R.H.)

| Preparations | Aspect | | | |
|---|---|---|---|---|
| | T0 | 2 Days | 15 Days | 1 Month |
| Glycerol:Water 30:70 | Slightly opalescent dispersion | Presence of a precipitate | N/A | N/A |
| Glycerol:Water 50:50 | Apparent clear and colourless solution | Slightly opalescent dispersion | N/A | N/A |
| Glycerol:Water 70:30 | Clear and colourless solution after 40 min | Clear and colourless solution | Clear and colourless solution | Clear and colourless solution |
| Glycerol:Water 85:15 | Clear and colourless solution after 30 min | Clear and colourless solution | Clear and colourless solution | Clear and colourless solution |
| Glycerol | Clear and colourless solution | Clear and colourless solution | Clear, slightly yellow solution | N/A |

N/A = Not available

Chemical stability data of T4 dissolved in glycerol:water mixtures with 70:30 w/w, 85:15 w/w ratios and 100% glycerol are given in the following table.

TABLE 10

T4 dissolved in glycerol:water mixtures with 70:30 w/w, 85:15 w/w ratios and 100% glycerol

| | | T0 | 15 DAYS | 1 MONTH |
|---|---|---|---|---|
| GLYCEROL:WATER 70:30 | T4 | 106% | 101.2% | 97.2% |
| | T3 | 0.10 | 0.56% | 0.48% |
| | T2 | <0.072 | <0.072 | <0.072 |
| | T3 reverse | <0.014 | <0.014 | <0.014 |
| | triac | <0.054 | <0.054 | <0.054 |
| | tetrac | <0.134 | <0.134 | <0.134 |
| | Single unknown imp. | <0.022% | 0.055% | 0.21% |
| | Total impurities | 0.10% | 0.61% | 0.69% |
| GLYCEROL:WATER 85:15 | T4 | 101.5% | 98% | 95.2% |
| | T3 | 0.099% | 0.44% | 0.41% |
| | T2 | <0.072 | <0.072 | <0.072 |
| | T3 reverse | <0.014 | <0.014 | <0.014 |
| | triac | <0.054 | <0.054 | <0.054 |
| | tetrac | <0.134 | <0.134 | <0.134 |
| | Single unknown imp. | <0.022% | 0.41% | 0.21% |
| | Total impurities | 0.10% | 1.26% | 0.62% |
| GLYCEROL 100% | T4 | 101.3% | 67.6% | 57.5% |
| | T3 | 0.081% | 0.14% | 0.11% |
| | T2 | <0.072 | <0.072 | <0.072 |
| | T3 reverse | 0.13 | 0.12% | <0.014 |
| | triac | <0.054 | <0.054 | <0.054 |
| | tetrac | <0.134 | 0.46% | 0.40% |
| | Single unknown imp. | 0.092% | 3.4% | 2.91% |
| | Total impurities | 0.37% | 4.87% | 3.96% |

Challenge test data of T4 dissolved in glycerol:water mixtures with 70:30 w/w. 85:15 w/w ratios and 100% glycerol are given in the following table.

| | CHALLENGE TEST |
|---|---|
| GLYCEROL:WATER 70:30 | complies |
| GLYCEROL:WATER 85:15 | complies |
| GLYCEROL 100% | complies |

T4 solubility and T4 chemical and microbiological stability in accelerated stability studies were monitored in order to reach an optimal balance of drug product characteristics. Glycerin:water ratios as low as 30:70 w/w and 50:50 did not guarantee the target T4 solubility, i.e., T4 concentrations as high as 200 μg/mL were not achievable since a precipitate or an opalescent dispersion was observed. When T4 was dissolved in 100% glycerol, a significant reduction of T4 assay (<70%) was observed after 15 days at 40° C.±2° C./75%±5% R.H.

The final selected formulation was a T4 solution in 85% glycerol w/w. In this mixture, T4 was freely soluble up to 200 μg/mL and was chemically stable in accelerated conditions. The outcome of the challenge test indicated that this solution was also microbiologically stable.

Although 70% glycerol showed T4 solubility and chemical stability similar to those observed with 85% glycerol, this latter concentration was selected for the product development. In fact, a slightly higher percentage of glycerol appeared to improve the solubilization rate of T4, and it is expected to better preserve T4 from precipitation at the higher concentrations and warrant microbiological stability.

Stability testing at 5° C., 25° C./60% R.H., 30° C./65% R.H. and 40° C./75% R.H. according to ICH conditions is currently ongoing on development batches of oral solutions of T4 dissolved in 85% glycerol at concentrations of 25, 50 and 100 μg/mL. After 9-month storage, this formulation is stable at all strengths at all of the above conditions.

It can be seen that all the tested samples in accordance with the invention, at substantially all doses, storage times and storage conditions, showed a consistent reduction of conversion in T4 to T3. The aims of the present invention are thus met.

Other objects, advantages and embodiments of the various aspects of the present invention will be apparent to those who are skilled in the field of the invention and are within the scope of the description. For example, but without limitation, structural or functional elements might be rearranged, or method steps reordered, consistent with the present invention. Similarly, features or methods may comprise a single instance or step, or a plurality of separate instances or steps. The features of the invention described in various embodiments are not meant to limit the possible types of elements that may be used in embodiments of aspects of the present invention, and other elements that may accomplish similar tasks may be implemented as well. Similarly, principles according to the present invention, and methods and systems that embody them, could be applied to other examples, which, even if not specifically described here in detail, would nevertheless be within the scope of the present invention.

The invention claimed is:

1. A pharmaceutical preparation of T4 thyroid hormone comprising a container pre-filled with a liquid pharmaceutical composition consisting essentially of:
   T4 thyroid hormone dissolved in an alcohol-free and preservative-free solution of 85% glycerol in water, and
   optionally T3 thyroid hormone in an amount of less than 2.5%;
   wherein the container is a single dose plastic container.

2. The pharmaceutical preparation of claim 1, wherein the liquid pharmaceutical composition contains optionally T3 thyroid hormone in an amount of less than 2.0%.

3. The pharmaceutical preparation of claim 2, wherein the liquid pharmaceutical composition contains optionally T3 thyroid hormone in an amount of less than 1.8%.

4. The pharmaceutical preparation of claim 1, wherein the T4 thyroid hormone to glycerol weight ratio in the alcohol-free solution is in the range from about 4 to about 400 ppm.

5. The pharmaceutical preparation of claim 1, wherein a single dose unit is 5 to 350 μg of T4 thyroid hormone.

6. The pharmaceutical preparation of claim 5, wherein a single dose unit is 5 to 250 μg of T4 thyroid hormone.

7. The pharmaceutical preparation of claim 1, wherein the plastic container has a thickness of between about 150 and about 1000 μm.

8. The pharmaceutical preparation of claim 7, wherein the plastic container has a thickness of between about 200 and about 800 μm.

9. The pharmaceutical preparation of claim 1, wherein the plastic container is made of one-component LDPE plastic.

\* \* \* \* \*